United States Patent [19]
Boute

[11] Patent Number: 5,330,511
[45] Date of Patent: Jul. 19, 1994

[54] DUAL CHAMBER PACEMAKER WITH AUTOMATICALLY OPTIMIZED AV DELAY

[75] Inventor: Willem Boute, Dieren, Netherlands

[73] Assignee: Vitatron Medical B.V., Dieren, Netherlands

[21] Appl. No.: 5,744

[22] Filed: Jan. 19, 1993

[51] Int. Cl.$^5$ ............................................. A61N 1/368
[52] U.S. Cl. ........................................ 607/25; 607/17; 607/27
[58] Field of Search ................ 607/17, 19, 25, 27, 607/9

[56] References Cited

U.S. PATENT DOCUMENTS

| | | | |
|---|---|---|---|
| 4,303,075 | 12/1981 | Heilman et al. | 128/419 PG |
| 4,467,807 | 8/1984 | Bornzin | 128/419 PG |
| 4,527,568 | 7/1985 | Rickards | 128/419 PG |
| 4,539,991 | 9/1985 | Boute et al. | 128/419 PG |
| 4,554,921 | 11/1985 | Boute et al. | 128/419 PG |
| 4,674,518 | 6/1987 | Salo | 128/695 |
| 4,686,987 | 8/1987 | Salo et al. | 128/419 PG |
| 4,856,524 | 8/1989 | Baker, Jr. | 128/419 PG |
| 4,920,965 | 5/1990 | Funke et al. | 128/419 PG |
| 4,951,667 | 8/1990 | Markowitz et al. | 128/419 PG |
| 4,972,834 | 11/1990 | Begemann et al. | 607/25 |
| 5,086,774 | 2/1992 | Duncan | 607/9 |
| 5,144,950 | 9/1992 | Stoop et al. | 607/9 |
| 5,247,929 | 9/1993 | Stoop et al. | 607/14 |

Primary Examiner—William E. Kamm
Assistant Examiner—Kennedy J. Schaetzle
Attorney, Agent, or Firm—Woodcock, Washburn, Kurtz, Mackiewicz & Norris

[57] ABSTRACT

The dual chamber system and method of operation contains an automatic test for determining an optimum AV interval at a test frequency such as LRL. In a preferred embodiment the test is carried out at nighttime, wherein the implanted pacer is set to asynchronous operation at LRL, and AV interval is sequenced through a range from a predetermined $AV_{min}$ to a predetermined $AV_{max}$. The QT interval corresponding to each respective AV interval is determined and stored; the QT data is analyzed to determine the maximum QT interval; and the optimum AV is determined at that which corresponds to the maximum QT. The optimum AV interval thus found is incorporated into the pacer memory for use in timing out AV interval. The optimum AV data may be utilized for determining $AV=f_s(rate)$ for calculating AV interval following each AS, as well as $AV=f_p(rate)$ for calculating AV interval following an atrial pace. Alternately, a test can be performed to determine whether an incremental adjustment of AV delay is indicated. In accordance with the invention, a DDDR pacer with automatic AV delay control can be achieved, without need for an extra sensor.

26 Claims, 6 Drawing Sheets

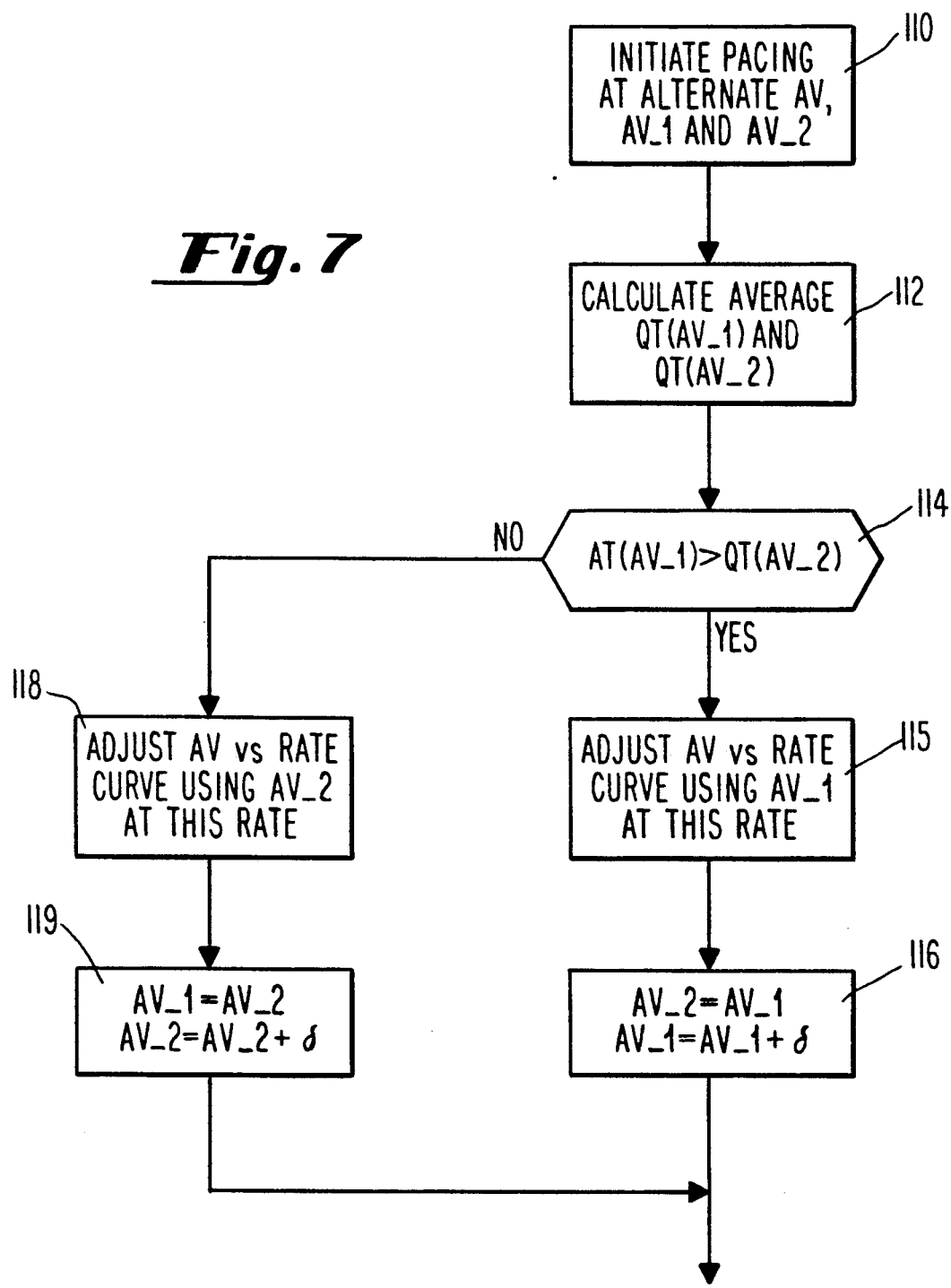

DUAL CHAMBER PACEMAKER WITH AUTOMATICALLY OPTIMIZED AV DELAY

BACKGROUND OF THE INVENTION

1. Field of the Invention

This invention relates to dual chamber cardiac pacemakers and pacemaker systems and, more particularly, to an implantable dual chamber pacemaker having automatic capability of determining an optimum AV interval for the patient and adjusting the pacer AV interval to the determined optimal value.

2. Description of the Prior Art

The advantages of dual chamber pacing, and more particularly pacing in different modes which are selected in response to different patient conditions, is now well recognized in the art. Early pacing systems were solely ventricular, and were sufficient for management of patient with complete heart block and Stokes-Adams attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (AV) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" techniques.

Another form of A-V or dual chamber pacer that has been utilized is the sequential pacemaker (DVI), which paces both the atrium and the ventricle with an appropriate AV delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et al., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. No. 4,527,568, and U.S. Pat. No. 4,920,965. However, as a general rule it is desirable to operate in a synchronized mode as much as possible, wherein an atrial sense (AS) is followed by a ventricular pace pulse (VP) which is timed to occur at an AV interval, or delay, after the AS. Likewise, if the pacemaker is operating in a mode where it is delivering both paced atrial and ventricular pace pulses, it is desired to have the VP follow the atrial pulse (AP) by an optimized AV interval.

It is known in the prior art that it is desirable to set the AV interval as a function of rate, e.g., as a function of sensed atrial rate or pacing rate. See U.S. application Ser. No. 830,656, Dual Chamber Pacemaker With AV Extension and PMT Control, filed Feb. 4, 1992 and assigned to the same assignee as this application; and Baker, U.S. Pat. No. 4,856,524. Thus, at lower atrial rates (corresponding to a longer A-A interval) the AV interval is desirably longer; and at higher atrial rates (corresponding to a shorter A-A interval) the AV interval is preferably shorter. Further, it is known in the prior art that pacing parameters such as AV interval can be programmed externally.

The prior art also shows an attempt to adjust AV interval in a pacemaker as a function of a sensed variable. See U.S. Pat. No. 4,303,075, wherein AV delay is modified in accordance with a sensed measure of stroke volume. However, this disclosure deals with a fixed rate pacer, and does not suggest how AV delay can be optimzied for a rate adaptive pacer. U.S. Pat. No. 4,686,987 discloses a technique for determining stroke volume and for controlling pacing rate as a function of stroke volume, but makes no suggestion of how to adjust AV delay in a rate adaptive pacer. There thus has remained a need for a pacing system that is capable of dynamic automatic adjustment of AV delay, i.e., a DDDR system where AV delay is adjustable through the pacing rate range.

DEFINITION OF THE PROBLEM AND SOLUTION PROVIDED BY THE INVENTION

The relationship between desired AV interval and heart rate not only varies from patient to patient but can vary with time for any given patient in which a dual chamber pacemaker has been implanted. There is thus a need for a system and method of periodically determining the optimum relationship between AV interval and pacing rate for a patient at one or more pacing rates, and automatically adjusting the relationship between atrial rate and AV delay in response to the determination. Particularly for a rate adaptive pacer, there is a need to automatically optimize AV delay, and preferably to do so without extra sensors.

Prior clinical studies have shown that the atrial contribution, or synchrony between atrium and ventricle, is most important at lower heart rates. At high heart rates the duration of the AV delay is less important, i.e., less of a factor in optimizing hemodynamic response. In pacemaker terminology, this means that for dual chamber operation near the lower rate limit, such as when the patient is at rest, the AV delay is more critical in optimizing the hemodynamics. Thus, when either the natural atrial rate or one or more sensors (as in a DDDR pacemaker) drive the heart rate higher, the AV delay introduced by the pacemaker can be reduced in accordance with a predetermined curve; the slope of the curve is less important than the fixed point on the curve representing AV delay at lower rate limit (LRL). What has not heretofore been available in an implantable pacemaker is a means to automatically test to see whether the curve representing the relationship between heart rate and AV delay is optimized in terms of the patient's hemodynamics. It is particularly desirable to find a way to adjust the relationship between heart rate and AV delay at lower rates, including LRL.

Applicant has discovered that measurement of the QT interval of the patient provides the capability of finding out whether AV delay is optimized at a given heart rate. It is known that QT interval can be used as a measure of heart demand, i.e., whether the heart wants to pump more or less blood. This is the basis of the QT pacemaker, wherein a shortened QT interval is used to adjust the pacing rate upward to a higher rate, and a lengthened QT interval indicates a lower pacing rate. See U.S. Pat. No. 4,228,803, Rickards, which discloses a rate adaptive pacemaker based on the QT principle. However, I have now further observed that QT interval varies in a patient who is paced at a given rate, depending upon whether pacing is single chamber or dual chamber. Thus, I made QT interval measurements on a patient having an implanted DDD pacemaker, recording QT interval as a function of rate, first during VVI mode pacing and then during DDD mode pacing. Both QT interval measurements showed typical rate dependency: when the heart rate increases, then QT interval decreases. The patients were completely at rest during the measurements, thereby avoiding any influence of catecholamines. However, the results showed that the QT interval during DDD pacing consistently had slightly longer values, i.e., at each pacing rate the QT interval for DDD pacing was slightly longer than the QT interval for VVI pacing. The explanation that is suggested is that during VVI pacing the hemodynamics are worse, i.e., less efficient, than during DDD pacing. The QT interval reflects this situation by showing a relatively shorter value for VVI pacing, indicating that the heart is calling for more blood than in the more efficient synchronous mode.

Following the above observation, I measured QT intervals in two patients, each having a DDD pacemaker. In each case the patient was completely at rest, avoiding any influence of catecholamines on the QT interval. The AV delay was programmed to change in small steps from a relatively short minimum interval to a relatively long interval, e.g., from 75 to 400 ms in steps of 25 ms. After each change there was a three-minute waiting period for stabilization, after which the QT interval was measured corresponding to the AV delay. Pacing rate (atrial pacing) was held constant, avoiding any influence of heart rate on the QT interval. Therefore, the influence of the AV delay only on the QT interval could be studied. The data for each patient showed that QT first rose as AV delay was lengthened, and then dropped for even longer AV intervals. The longest QT interval is indicated as corresponding to the hemodynamically optimum AV interval. From this, it is suggested that a pacemaker can incorporate means for periodically performing a test to determine the optimum AV delay corresponding to a given rate such as LRL, which optimum value can be utilized by the pacemaker. Such a test can be run, for example, at night time, when the patient is at rest and his or her heart rate is at LRL in any event.

SUMMARY OF THE INVENTION

In accordance with the above observations, there is provided a dual chamber pacemaker system and method of operation of same wherein the pacemaker AV interval is adjustable in response to data representing an optimized AV interval. The pacemaker incorporates a test procedure, preferably microprocessor-controlled, for pacing both chambers of the patient's heart at night at a fixed rate corresponding to LRL, varying the AV delay and measuring QT interval corresponding to each AV delay, and then determining the maximum QT interval. Since the maximum QT interval corresponds to the hemodynamically optimum condition, the corresponding AV delay is stored and utilized when and as the pacemaker returns to the normal dual chamber operation. If the pacemaker utilizes a constant AV delay, the determined optimum interval is utilized. Alternatively, the pacemaker can be programmed to vary AV delay as a function of sensed or paced atrial rate, in which case the determined optimum value of AV delay at LRL is used in establishing the correlation between AV and heart rate. In yet another alternative, respective different correlation functions between heart rate and AV delay can be utilized, depending upon whether the atrial event is an atrial sense or atrial pace, in order to compensate for the latency between the AP and the actual atrial contraction.

In another preferred embodiment, adaptable to a rate adaptive pacer, AV delay can be optimized wherever the pacer is operating within its rate range, i.e., anywhere between LRL and URL. This is done by determining changes in a physiological variable that can be substantially solely attributed to variation in AV delay. For example, a variation in QT level is determined that is substantially free of the effect of QT dependence on rate and substantially reflective of variations in AV delay. The use of QT as a physiological variable also permits AV delay adjustment in a DDDR pacer without need of an extra sensor, i.e., with only normal pacing leads for delivering pace pulses and sensing heart signals.

BRIEF DESCRIPTION OF THE DRAWINGS

FIG. 7 is a flow diagram of another embodiment for dynamically determining an adjustment of AV delay.

DESCRIPTION OF THE PREFERRED EMBODIMENTS

Figure 1:
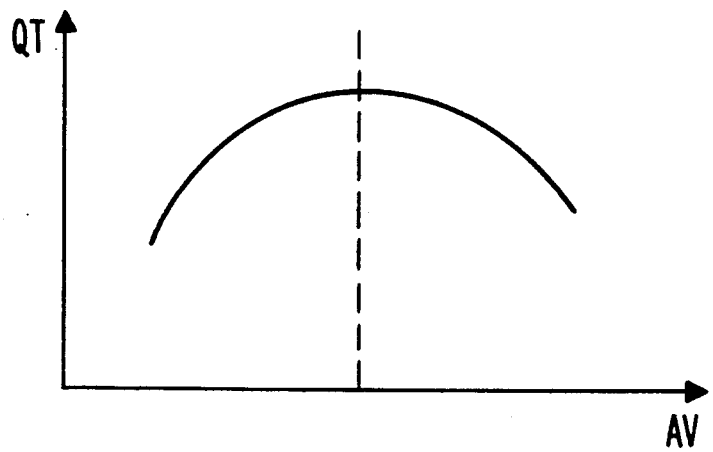
FIG. 1 is a curve illustrating the variation of QT interval versus AV delay for a patient paced in both the atrium and the ventricle at a fixed pacing rate.

Referring now to FIG. 1, there is a shown a representative graph acquired by varying the AV interval in a patient being paced at a fixed rate in both the atrium and ventricle, and measuring the QT interval corresponding to each AV interval. These curves reflect a statistical fitting to the actual data, and in each case lend to a determination of the peak of the curve, which corresponds to the optimized AV interval. As used herein, the optimum or optimized AV interval corresponds to about the peak of the curve; it is not necessary to find the exact peak in order to gain a significantly improved pacemaker response. Although the invention is illustrated by use of QT as the preferred hemodynamic variable, it is to be understood that other variables may be used within the scope of the invention. Thus, the pacemaker may include means for determining stroke volume, depolarization slope, pre-ejection interval, dp/dt, etc., each of such variables being equivalent to QT as a hemodynamic variable used in this invention.

Figure 2:
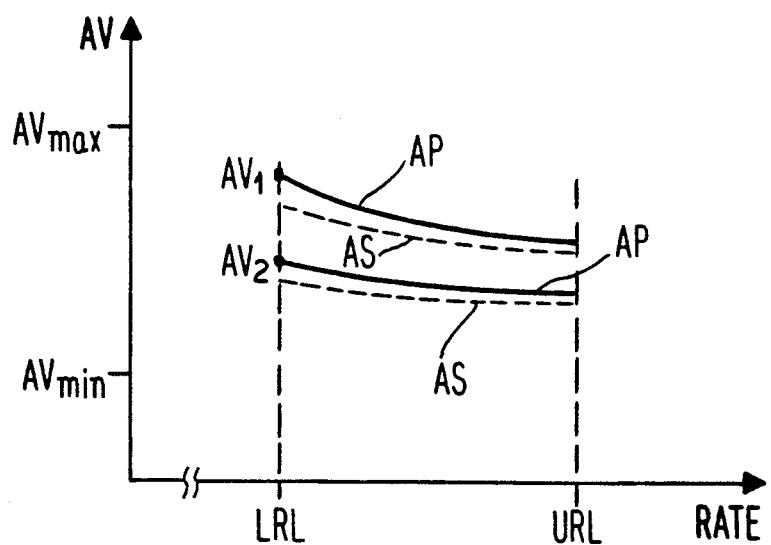
FIG. 2 is a representation of curves showing the relationship between AV interval and heart rate.

Assuming that a test is performed resulting in data as represented in FIG. 1, the optimized AV interval data can be used to adjust the AV interval used in dual chamber pacing. As discussed above, AV interval may preferably be a function of atrial rate, i.e., $AV = f(rate)$. In FIG. 2, rate is plotted on the horizontal axis, and AV interval is plotted on the vertical axis. The pacemaker is preferably programmed with a predetermined $AV_{min}$ and predetermined $AV_{max}$, and the $AV = f(rate)$ curve is positioned between the rate limits of LRL and URL. In FIG. 2, a first solid line is shown, which may be illustrative of $AV = f(rate)$ before the test. For this curve, AV at LRL is shown as $AV_1$. Assuming that the test is done at LRL, a new optimized value of $AV_2$ is determined at LRL, and shown by a second solid line indicating that the optimized AV at LRL is a lower value. In a simplified arrangement, the slope of the curve between the rate limits of LRL and URL may be held the same, such that the new curve is determined by repositioning of the value at LRL. Other more complex modifications are within the scope of the invention. Still referring to FIG. 2, dashed lines are shown which represent curves of $AV_s = f(rate)$, where $AV_s$ is the value of AV to be used following an AS for the embodiment where different values are used following atrial sense and atrial pace events.

Figure 3:
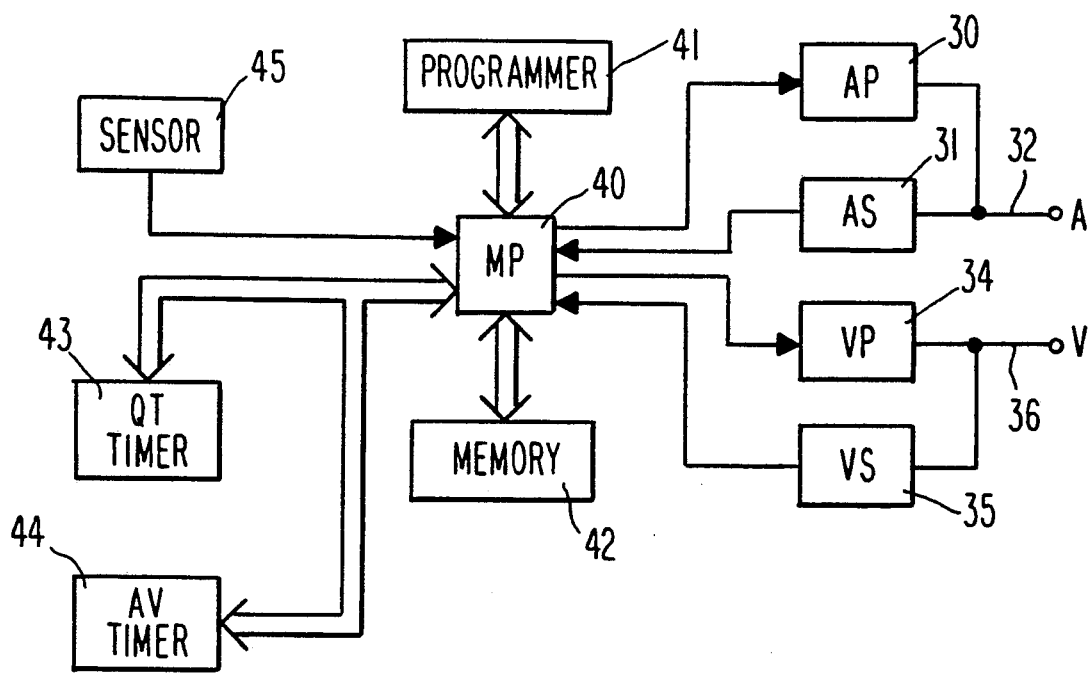
FIG. 3 is an overall block diagram of the primary components of a pacemaker system in accordance with this invention.

Referring now to FIG. 3, there is shown a block diagram illustrative of the major components of a pacemaker system in accordance with this invention. The atrial pulse generator 30 is triggered by timing signals, preferably from a microprocessor 40, for generation of atrial pulses. The atrial pulses are delivered through a lead 32 to the patient's atrium. Lead 32 also connects sensed atrial signals (AS) to atrial sense circuitry 31. The output of circuitry 31 is inputted into microprocessor 40. In a similar fashion, a ventricular pulse generator 34 and a ventricular sense circuit 35 are connected to a ventricular lead 36, for delivering ventricular pace pulses (VP) to the ventricle, and for receiving and detecting ventricular sense (VS) signals respectively. Generator 34 is triggered by a timing signal from microprocessor 40, while the output of sense circuit 35 is inputted to microprocessor 40. Thus, microprocessor 40 controls the timing of delivery of pace pulses to either or both the atrium and the ventricle; and receives sense signals which are used in controlling pacemaker operation, including timing of delivered signals. Also, lead 36 delivers T wave signals which are amplified through VS 35 and connected through to microprocessor 40. A programmer 41 is used for external programming. Microprocessor 40 controls and receives information from QT timer 43, for determining QT interval, in a well known manner. Likewise, a sensor or plurality of sensors 45 may be used, for a DDDR pacemaker, the signals from which are inputted into microprocessor 40 for rate responsive control. As is known, QT interval can be measured without an extra sensor. Also in a conventional manner, microprocessor 40 utilizes memory 42 suitably in the form of RAM and ROM, for storing data, holding subroutines, etc. An AV timer 44 is illustrated, controlled by microprocessor 40, for timing out the AV interval.

Figure 4A:
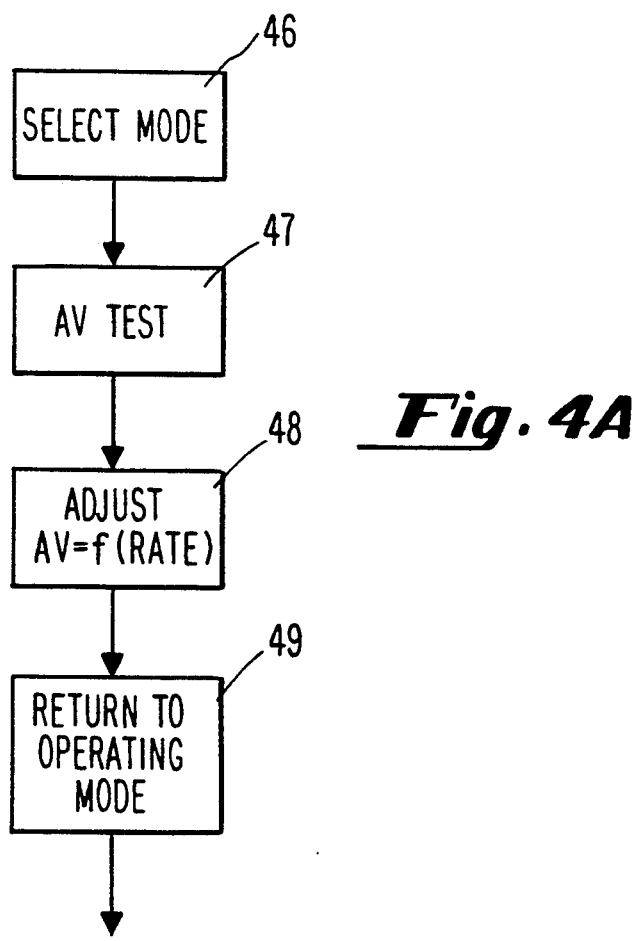
FIG. 4A is a simplified block diagram showing the basic steps of entering and exiting the test mode for determining optimized AV interval in accordance with this invention.

Referring to FIG. 4A, there is shown a simplified block diagram of the method of carrying out an AV test in accordance with this invention. At block 46, the pacemaker selects the mode of operation. This is standard procedure, and in an implantable DDD pacemaker the mode may be programmed from external programmer 41, or may be automatically switched in accordance with diagnostic data determined by the pacemaker. At block 47, the pacemaker goes into the AV test mode, wherein each chamber is paced at a fixed rate. The test mode may be initiated on any programmed basis, as selected by the physician. For example, a preferred arrangement is to enter the test mode at nighttime, which can be determined by an internal pacemaker clock which is controlled by the microprocessor. At nighttime, when the patient's body metabolism is low, the heart rate is presumed to be at or below the lower rate limit, such that the test is preferably carried out at LRL. Alternately, the test can be initiated any time the sensor indicates the patient is at or below LRL. Thus, the invention is not limited as to initiation of the test, and can be initiated in accordance with any predetermined criteria. Following the test mode, as shown at 48, the pacemaker automatically adjusts $AV = f(rate)$, in accordance with the determination of an optimized AV interval made at block 47. The pacemaker then returns to the chosen operating mode, as indicated at block 49.

Figure 4B:
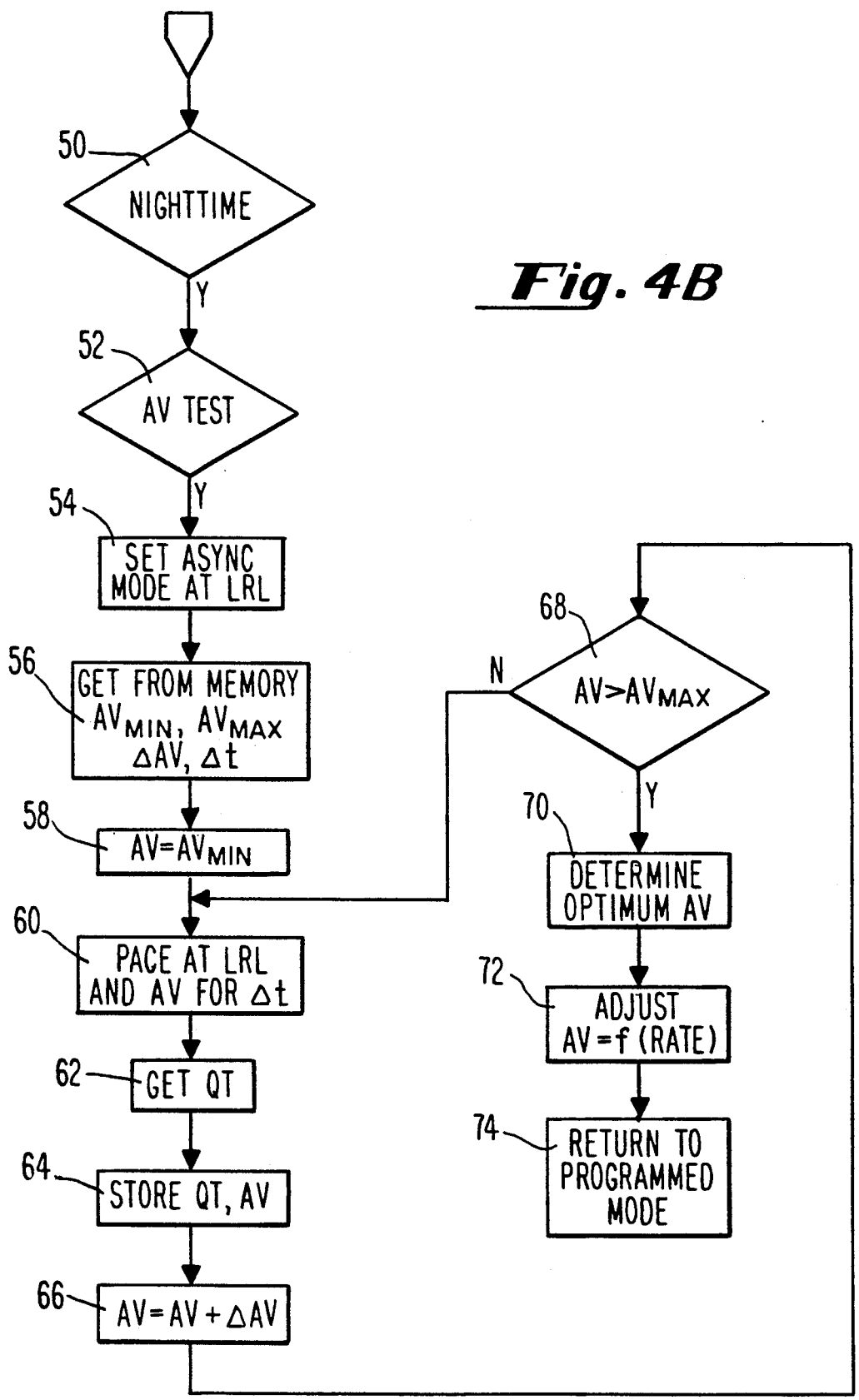
FIG. 4B is a more detailed flow diagram illustrating steps of the test for determining optimized AV interval in accordance with this invention.

Referring now to FIG. 4B, at block 50 the pacemaker determines whether it is nighttime or whether the sensor indicates LRL, such that the AV test can be initiated. If yes, a flag may be set, which is not reset until the clock has timed out 24 hours. The program goes to block 52, where it is determined whether AV test is desired. Thus, the pacemaker could be programmed to perform the test at intervals of less than every night, once a week, once every ten days, etc. If the test is to be performed, the pacemaker goes to block 54, and sets the mode to async, at a rate of LRL. At block 56, the pacemaker gets the information necessary to perform the test, from memory 42. This information includes $AV_{min}$; $AV_{max}$; $\Delta AV$ (the step by which AV is incremented for the next determination of QT interval); and $\Delta t$, which is the period of time that the pacemaker stabilizes after change in AV and before measuring QT.

At block 58, AV is set equal to $AV_{min}$, the starting point for the test. At block 60, the pacemaker paces at LRL and with the set AV interval, for time $\Delta t$. Following the timeout of $\Delta t$, the pacemaker gets the QT interval, as indicated at 62. Determination of QT interval is done in the standard manner, as is well documented in the patent literature. As a matter of design choice, only one QT interval may be obtained; a series of intervals may be obtained and averaged; or any equivalent sampling of QT may be used. At 64, the data representing the corresponding QT and AV are stored in memory. At 66, AV is incremented by $\alpha AV$, and at 68 the pacemaker checks to determine whether AV is greater than $AV_{max}$. If no, the program branches back to block 60, and paces at the new AV, to get the next QT. The pacemaker cycles through this subroutine until AV is determined to be greater than $AV_{max}$ at 68, at which time it branches to block 70.

At block 70, the pacemaker determines the optimum AV interval, corresponding to LRL, from the data stored in memory. This can be done in different ways, the precise algorithm which is utilized being a matter of choice, such that any determination is within the scope of this invention. Thus, the simplest algorithm would involve searching for the greatest QT interval. On the other hand, a more accurate algorithm involves a statistical analysis of the data to generate a curve which is fit to the data, so as to determine where the first derivative of the curve is equal to zero, thereby more precisely locating an optimized AV interval.

The above-described test measures the entire AV versus QT curve (FIG. 1). This requires a long measurement period. A simpler and faster method is to change the AV delay to one step (e.g. step of 25 ms) longer and one step shorter than the presently active value. If during one of these steps a longer QT interval is measured, the active AV delay should be changed by one step (could be a different step size) in that direction. If the presently active AV delay has the optimal value, both measurements will yield a shorter QT interval and therefore no adaption is necessary. It is preferable that the presently active AV delay value only be adapted by a single step per measurement (per day). This avoids large variations in the event that, for whatever reason, a measurement yields incorrect information.

Following determination of the AV interval, the program adjusts the rate correlation function, as indicated at 72. For the example where optimized AV is determined only at LRL, the adjustment may involve simply shifting the entire curve either up or down, corresponding to the detected change at LRL. As discussed above, other more complex curves may be utilized. It is clear, however, that the curve cannot be adjusted so as to go beyond the limits of $AV_{min}$ or $AV_{max}$, such that a simple shift up or down may not be possible. Any desired algorithm for adjustment of $AV = f(rate)$ may be used, and is within the scope of this invention. However, as indicated above, it is preferable that AV delay be changed by only a predetermined increment per day.

Figure 5A:
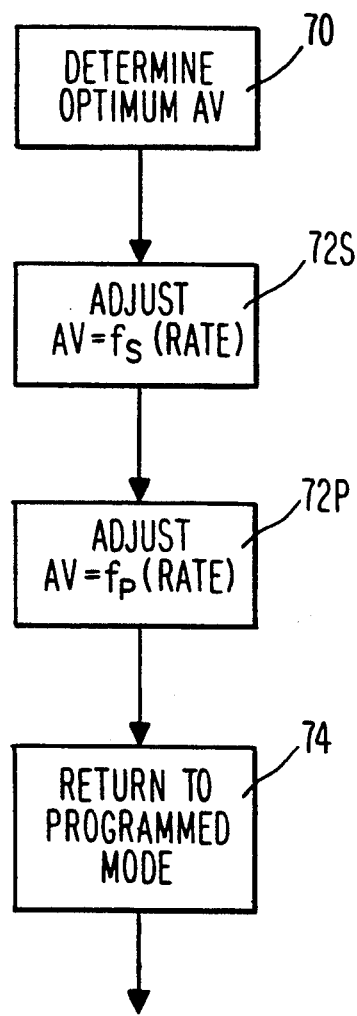
FIG. 5A is a partial flow diagram illustrating the adjustment of the AV interval to be used following an AS, and adjustment of the AV interval to be used following an AP.

Referring now to FIG. 5A, there is shown a simplified partial flow diagram of the system and method of this invention wherein respective different AV curves are utilized. Following determination of the optimum AV at block 70, the routine proceeds to use the newly acquired optimum AV to adjust correlation with rate which is to be used following an AS, i.e., $AV = f_s(rate)$, as indicated at block 72S. Following this, a similar but different adjustment is made for the curve $AV = f_p(rate)$ as indicated at block 72P. The pacemaker then returns to the programmed mode.

Figure 5B:
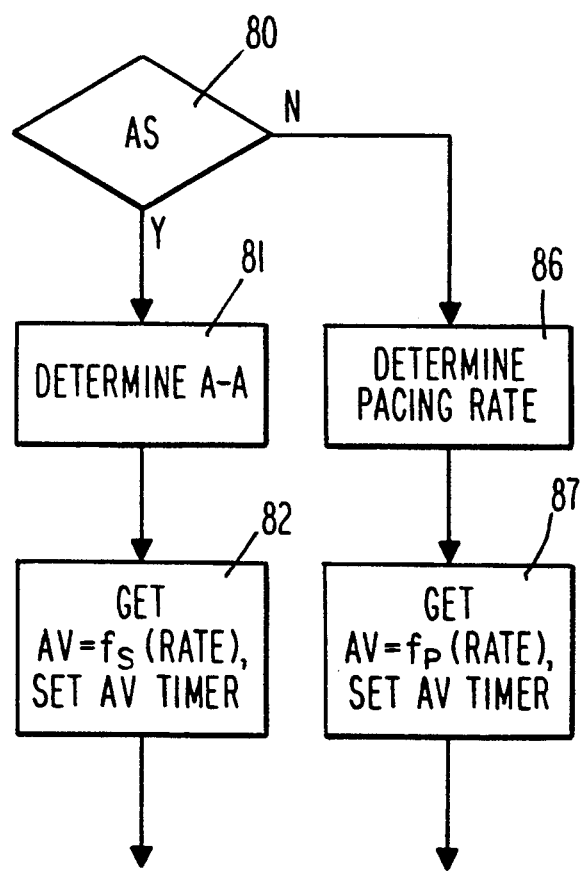
FIG. 5B is a partial flow diagram illustrating the selection of AV interval following an AS or an AP.

Referring to FIG. 5B, there is shown a partial simplified block diagram of pacemaker operation following an atrial event. At 80, it is determined whether the last atrial event was AS or AP. If AS, the pacemaker determines the last AA interval, which is representative of atrial rate. At block 82, the pacemaker utilizes the stored curve $AV = f_s(rate)$ to set the AV timer corresponding to the atrial rate. If, at 80 it is determined that the atrial event was an AP, the pacemaker gets the pacing rate at 86, and at 87 gets the curve $AV = f_p(rate)$, and sets the AV timer to the determined value of AV.

Figure 6A:
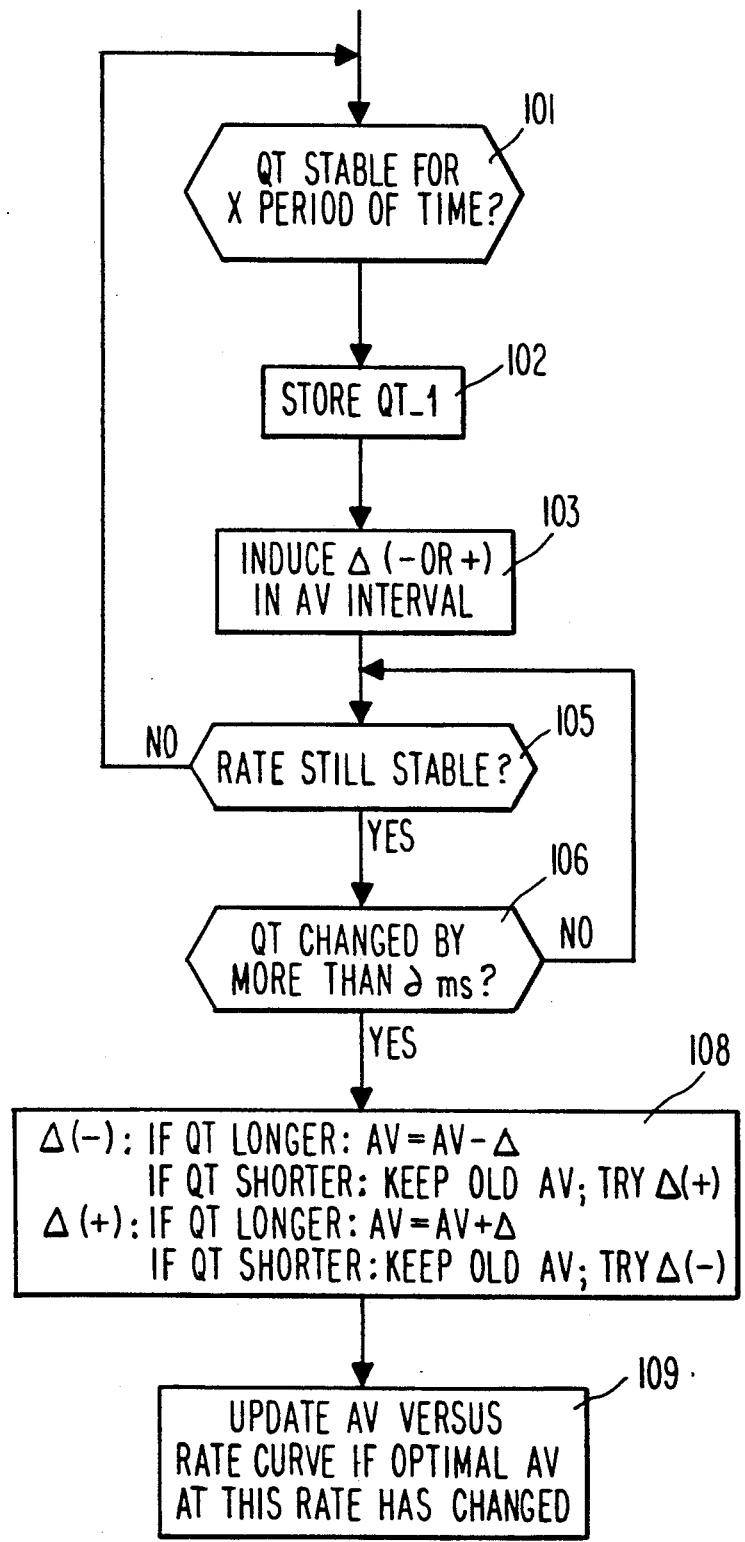
FIG. 6A is a flow diagram illustrating an alternative means for determining a desired adjustment of AV interval at any stable rate within the pacer rate range.
Figure 6B:
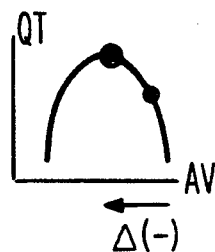
FIG. 6B illustrates a decrease in AV delay in response to an increase in QT.
Figure 6C:
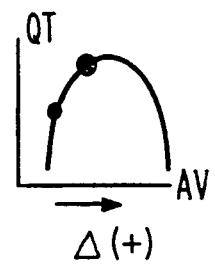
FIG. 6C illustrates an increase in AV delay in response to an increase in QT.

Referring now to FIGS. 6A–6D, there is shown an alternate embodiment for AV optimization at any rate, i.e., not just at the lower rate limit. The embodiment is based on the observation that QT interval varies with rate, such that if the rate is not substantially stable, a variation in QT would not be an accurate predictor of desired AV interval. It is necessary to detect a situation where heart rate, and thus metabolic demand, do not modulate the QT interval. In the embodiment of FIG. 6A, the pacemaker first looks for a period of time where the QT interval has been stable, as illustrated at 101. This condition can exist at a heart rate well above LRL, when the heart is either sensor or atrial driven. If such a period of stable rate and QT interval is detected, a change in the AV interval can be made for the purpose of sensing change in QT attributable to the change in AV. As long as the heart rate does not vary during the time of changed AV interval, the QT measurement is valid for this purpose, i.e., it has not been influenced by rate and/or metabolic demand. As with the prior embodiments, if the QT interval shortens, then the previous AV interval was more optimal, and it can be concluded that direction of AV change is not the direction in which the AV versus rate curve should be adjusted. However, if the QT interval lengthens in response to the change in AV, then the AV versus rate curve should be adjusted in accordance with the changed AV interval.

Figure 6D:
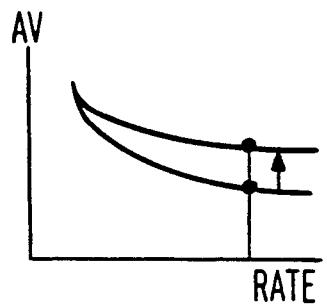
FIG. 6D illustrates adjustment of the curve of AV versus rate.

Continuing with FIG. 6A, the value of the stable QT, QT_1, is stored at 102. AV interval is then changed by an amount $\Delta$, either incremented (+) or decremented (−), as shown at 103. The pacemaker preferably holds this condition for an increment of time, to stabilize. The program proceeds to block 105, where it is determined whether the rate is still stable. If no, the program branches back to block 101 to try again. If the rate has remained stable, then at block 106 QT is measured and compared with QT_1, to see if it has changed by more than $\partial$ ms. If no, meaning that there was not significant change in QT, the program loops back to 105. If yes, the program proceeds to 108 where it carries out logic to determine whether the AV interval should be incremented or decremented. If the AV interval was decremented, then a longer QT means that the decremented AV interval should be used. If QT is shorter, this a worse condition, and the prior AV interval should be kept. However, in this latter situation, it is then known that the pacemaker should rerun the test, following increasing the AV interval. This information is acted upon at block 103 next time the pacemaker loops through the routine. Block 108 also shows the logic following incrementing AV interval. At block 109, the curve of AV versus rate, as shown in FIG. 6D, is adjusted in accordance with the analysis at block 108.

Referring now to FIG. 7, there is shown a further alternate embodiment optimizing AV interval at substantially any rate within the pacing rate range, under dynamic conditions where rate is not necessarily stable. As discussed above, the problem in this circumstance is that a changing rate will itself cause a change in QT, which change must be effectively filtered out so that a sensed change in QT is attributable to a change in AV. This is done by alternating the AV interval substantially constantly between a first interval $AV\_1$ and a second interval $AV\_2$. Thus, at any given rate, where $AV\_1 = F(rate)$, $AV\_2$ may be calculated as $AV\_1$ plus or minus $\Delta AV$, or $AV\_1$ and $AV\_2$ may be shorter and longer than the currently used AV. On alternating cycles, the AV delay is first $AV\_1$ and then $AV\_2$, as indicated at block 110. At 112, average values of each of QT ($AV\_1$) and QT ($AV\_2$) are determined over a plurality of pacemaker cycles, or a given length of time. In this example, $AV\_1$ is shorter than $AV\_2$. Even though there may have been a change in metabolic demand during this period of time, the difference between the averages is indicative of whether AV delay should be changed. At Block 114, QT ($AV\_1$) is compared to QT ($AV\_2$). If QT ($AV\_1$) is greater than QT ($AV\_2$), the program branches to block 115 where the AV versus rate curve is adjusted by using $AV\_1$ at the current rate. Then, at block 116, $AV\_2$ is set equal to $AV\_1$, and $AV\_1$ is incremented by an arbitrary amount $\partial$. Note that AV is thus optimized incrementally, without attempting to find an optimal value. If, at block 114, QT ($AV\_1$) is not greater than QT ($AV\_2$), then the program branches to block 118, and the curve is adjusted using the value of $AV\_2$ at this rate. Following this, $AV\_1$ is set equal to $AV\_2$, and $AV\_2$ is incremented by $\partial$.

It is seen from the above description that there is provided a system and method for automatically testing to determine a patient-optimized AV interval, at one or more heart rates, and for automatically adjusting the AV interval used by the pacemaker for dual chamber synchronous pacing operation. The invention has been illustrated by a system which measures QT interval as the hemodynamic variable that is compared to AV interval, but other hemodynamic variables are equally useful and within the scope of the invention. Thus, as with the QT interval, any variable can be used so long as change in the variable can be substantially attributable to change in AV interval. In the preferred embodiment of a DDDR pacing system, QT is the variable chosen for controlling pacing rate and for determining how to optimize AV interval. The system thus provides the advantage of providing both rate responsiveness and automatic optimization of AV interval without the need of an extra sensor. However, utilization of an extra sensor, or combination of QT and sensor input, for rate control and/or AV delay control, is within the scope of the invention.

What is claimed:

1. A dual chamber pacing system having AS means for sensing atrial beats (AS), AP means for generating and delivering atrial pace pulses (AP), VS means for sensing ventricular beats (VS), VP means for generating and delivering ventricular pace pulses (VP), and AV means for timing an AV interval following an atrial event (AS or AP) and for controlling delivery of a VP at an interval according to the function $AV = f(rate)$ following a said atrial event and in the absence of a VS, comprising determining means for automatically determining an optimized AV interval corresponding to at least one predetermined pacing rate, and adjusting means for adjusting said function $AV = f(rate)$ to comprise said determined optimized AV interval at said predetermined pacing rate.

2. The dual chamber pacing system as described in claim 1, comprising rate responsive means for controlling pacing rate and wherein said AP and VP means generate pace pulses at a rate between a lower rate limit (LRL) and a upper rate limit (URL), and said predetermined pacing rate is said LRL.

3. The dual chamber pacing system as described in claim 2, wherein said AV means controls AV to vary as a function of rate in a predetermined relationship relative to the determined AV interval at LRL.

4. The pacing system as described in claim 1, wherein said determining means comprises means for delivering atrial and ventricular pace pulses at a fixed rate and varying means for varying the AV interval, and means for measuring the variation of at least one selected hemodynamic variable as a function of said varied AV interval.

5. The pacing system as described in claim 4, wherein said hemodynamic variable is QT interval.

6. The dual chamber pacing system as described in claim 1, wherein said AV means controls said AV to decrease as a function of increasing rate.

7. The dual chamber pacing system as described in claim 1, wherein said determining means comprises programmable test means for carrying out a test for determining optimum AV interval.

8. The dual chamber pacing system as described in claim 7, wherein said test means is programmed to carry out said test at nighttime.

9. The dual chamber pacing system as described in claim 7, wherein said test means comprises changing the value of AV by predetermined increments, while pacing both the patient's atrium and ventricle at LRL, and means for measuring and storing values of QT interval corresponding to each respective value of AV.

10. The system as described in claim 1, wherein said adjusting means adjusts AV as a different function of rate following AS and AP respectively.

11. The dual chamber pacing system as described in claim 5, wherein said determining means comprises means for selecting substantially the highest measured value of QT and determining the AV value that corresponds to said highest QT value as said optimum AV interval.

12. The dual chamber pacing system as described in claim 5, wherein said determining means comprises means for processing said QT measurements to determine the approximate maximum value of QT, and determining the AV value that corresponds to said approximate maximum QT value as said optimum AV interval.

13. A method of dual chamber operation by a pacing system implanted in a patient, said pacing system having atrial sense means for sensing natural atrial events (AS) and atrial pace means for delivering atrial pace pulses (AP), ventricular pace means for delivering ventricular pace pulses (VP), synchronizing means for controlling delivery of a said VP at an AV interval following either an AS or AP according to a function $AV = f(rate)$, said method of operation further comprising determining an optimum AV interval at at least one rate, and adjusting said function in accordance with said optimum AV interval, said determining step comprising:

switching said implanted pacing system into a mode wherein AP and VP pulses are delivered to the patient at a predetermined rate, each VP following a prior AP by an AV interval, testing the AV interval by adjusting the AV interval to a plurality of adjusted intervals, and determining a measure of the patient QT interval corresponding to each respective adjusted AV interval, and determining from said measures of QT intervals whether the AV interval at said predetermined rate should be changed, and changing the value of the AV interval corresponding to said predetermined rate in accordance with said testing.

14. The method as described in claim 13, comprising carrying out said test at nighttime.

15. A dual chamber pacemaker having means for sensing atrial heartbeats (AS) and for generating ventricular pace pulses (VP) each synchronized to a preceding AS, comprising means for determining the QT intervals following a series of delivered VPs, means for analyzing said QT intervals, and AV means for setting the AV interval between an AS and a following VP, said AV means having adjusting means for adjusting said AV interval as a function of said analyzed QT intervals.

16. A rate responsive dual chamber pacemaker having means for sensing atrial heartbeats (AS), means for generating atrial pace pulses (AP) at a rate variable through a rate range, means for generating ventricular pace pulses (VP) at a rate variable through said rate range, means for synchronizing a VP to a preceding AS, AV means for setting the AV interval between an AS or AP and a following VP, and variable means for sensing the value of a predetermined variable representative of patient cardiac hemodynamics, characterized by determining means for determining the variation of said predetermined variable with variation of AV interval, and said AV means having adjusting means for adjusting said AV interval in accordance with said determined variation.

17. The dual chamber pacemaker as described in claim 16, wherein said predetermined variable is QT interval.

18. The dual chamber pacemaker as described in claim 17, wherein said determining means comprises AV change means for changing said AV interval over a predetermined AV interval range while pacing both the atrium and the ventricle at a fixed rate.

19. The dual chamber pacemaker as described in claim 18, comprising means for limiting said adjusting means to adjusting AV interval by only a predetermined amount per adjustment.

20. The dual chamber pacemaker as described in claim 16, further characterized by initiating means for initiating said determining in accordance with predetermined criteria.

21. The dual chamber pacemaker as described in claim 20, wherein said initiating means determines when the patient heart rate is at or below a predetermined LRL.

22. The dual chamber pacemaker as described in claim 16, wherein said determining means comprises means for determining when said predetermined variable has been stable for a predetermined period of time, and means for initiating variation of AV interval only upon determination of said variable stability.

23. The dual chamber pacemaker as described in claim 16, further characterized by said determining means comprising varying means for varying said AV interval to alternate values over a plurality of pacing cycles.

24. A dual chamber pacemaker having means for sensing atrial heartbeats (AS), means for generating atrial pace pulses (AP), means for generating ventricular pace pulses (VP), lead means for delivering said pace pulses and sensing ventricular heartbeats (VS), means for synchronizing a VP to a preceding AS, AV means for setting the AV interval between an AS or AP and a following VP, variable means for sensing the value of a predetermined variable representative of patient cardiac hemodynamics, rate control means for controlling the rate of said ventricular pace pulses as a function of said variable, and characterized by change means for changing said AV interval in a predetermined manner, determining means for determining the change in said variable attributable to said AV interval change, and said AV means having adjust means for adjusting the AV interval in accordance with said attributable variable change.

25. The pacemaker as described in claim 24, wherein said rate control means controls said rate over at least a predetermined range, and wherein said change means is operative substantially through said range and said AV means adjusts said AV interval for the rate corresponding to which said variable change is determined.

26. The pacer as described in claim 24, further comprising means for determining said variable from said sensed ventricular heartbeats.

* * * * *